US008771503B2

(12) United States Patent
Cha et al.

(10) Patent No.: US 8,771,503 B2
(45) Date of Patent: Jul. 8, 2014

(54) PROCESS AND SYSTEM FOR RECOVERING OIL FROM TAR SANDS USING MICROWAVE ENERGY

(75) Inventors: Chang Yul Cha, Laramie, WY (US); Paul Gil Vergnani, Laramie, WY (US)

(73) Assignee: C-Micro Systems Inc., Saint-Lazare, Quebec ( * ) Notice: Subject to any disclaimer, the term of this patent is extended or adjusted under 35 U.S.C. 154(b) by 572 days.

(21) Appl. No.: 12/621,923

(22) Filed: Nov. 19, 2009

(65) Prior Publication Data

US 2011/0114470 A1 May 19, 2011

(51) Int. Cl.
*C07C 4/02* (2006.01)

(52) U.S. Cl.
USPC . 208/402; 208/400; 204/157.15; 204/157.62; 204/157.63; 204/157.69

(58) Field of Classification Search
USPC ......... 208/390, 402, 404, 427–428, 430, 435, 208/400; 204/157.15, 157.62–157.63, 204/157.69
See application file for complete search history.

(56) References Cited

U.S. PATENT DOCUMENTS

| | | | |
|---|---|---|---|
| 3,941,421 | A | 3/1976 | Burton, III et al. |
| 3,994,343 | A | 11/1976 | Cha et al. |
| 4,005,752 | A | 2/1977 | Cha |
| 4,014,575 | A | 3/1977 | French et al. |
| 4,036,299 | A | 7/1977 | Cha et al. |
| 4,076,312 | A | 2/1978 | Cha et al. |
| 4,086,962 | A | 5/1978 | Cha |
| 4,089,375 | A | 5/1978 | Cha |
| 4,105,072 | A | 8/1978 | Cha |
| 4,119,345 | A | 10/1978 | Bartel et al. |
| 4,126,180 | A | 11/1978 | Cha |
| 4,149,595 | A | 4/1979 | Cha |
| 4,149,752 | A | 4/1979 | Cha et al. |
| 4,150,722 | A | 4/1979 | Cha et al. |
| 4,156,461 | A | 5/1979 | Cha |
| 4,162,706 | A | 7/1979 | Cha |
| 4,163,475 | A | 8/1979 | Cha et al. |
| 4,166,721 | A | 9/1979 | Cha |
| 4,191,251 | A | 3/1980 | Cha |
| 4,192,381 | A | 3/1980 | Cha |
| 4,192,552 | A | 3/1980 | Cha |
| 4,224,990 | A | 9/1980 | Cha |
| 4,227,574 | A | 10/1980 | Cha |
| 4,263,970 | A | 4/1981 | Cha |
| 4,279,302 | A | 7/1981 | Cha |
| 4,983,278 | A | 1/1991 | Cha et al. |
| 5,041,209 | A | 8/1991 | Cha et al. |
| 5,087,269 | A | 2/1992 | Cha et al. |
| 5,164,054 | A | 11/1992 | Cha et al. |
| 5,171,406 | A | 12/1992 | Shang et al. |
| 5,198,084 | A | 3/1993 | Cha et al. |
| 5,246,554 | A | 9/1993 | Cha |
| 5,256,265 | A | 10/1993 | Cha |

(Continued)

FOREIGN PATENT DOCUMENTS

| | | | |
|---|---|---|---|
| CA | 1108081 | * 9/1981 | ............... C10G 1/04 |

*Primary Examiner* — Brian McCaig
(74) *Attorney, Agent, or Firm* — Norton Rose Fulbright Canada

(57) ABSTRACT

A process for recovering an oil from a tar sand, including the steps of drying the tar sand to produce a dried tar sand, mixing the dried tar sand with a microwave absorbent to produce a mixed sand, and cracking the mixed sand with microwaves to produce an oil vapor product containing the oil.

15 Claims, 3 Drawing Sheets

(56) References Cited

U.S. PATENT DOCUMENTS

| | | | | |
|---|---|---|---|---|
| 5,269,892 | A | 12/1993 | Cha | |
| 5,362,451 | A | 11/1994 | Cha | |
| 5,389,691 | A | 2/1995 | Cha et al. | |
| 5,451,302 | A | 9/1995 | Cha | |
| 5,470,384 | A | 11/1995 | Cha et al. | |
| 5,536,477 | A | 7/1996 | Cha et al. | |
| 5,688,332 | A | 11/1997 | Cha | |
| 5,735,948 | A | 4/1998 | Cha et al. | |
| 5,767,470 | A | 6/1998 | Cha | |
| 6,027,698 | A | 2/2000 | Cha | |
| 6,045,663 | A | 4/2000 | Cha | |
| 6,046,376 | A | 4/2000 | Cha et al. | |
| 6,187,988 | B1 | 2/2001 | Cha | |
| 6,207,023 | B1 | 3/2001 | Cha | |
| 6,284,202 | B1 | 9/2001 | Cha et al. | |
| 6,419,799 | B1 | 7/2002 | Cha | |
| 6,592,723 | B2 | 7/2003 | Cha | |
| 6,709,573 | B2 * | 3/2004 | Smith | 208/390 |
| 6,783,632 | B2 | 8/2004 | Cha | |
| 6,830,662 | B2 | 12/2004 | Cha | |
| 7,303,684 | B2 | 12/2007 | Cha | |
| 7,629,497 | B2 | 12/2009 | Pringle | |
| 2004/0031731 | A1 * | 2/2004 | Honeycutt et al. | 208/402 |

* cited by examiner

PROCESS AND SYSTEM FOR RECOVERING OIL FROM TAR SANDS USING MICROWAVE ENERGY

FIELD OF THE INVENTION

The present invention relates to recovering oil from tar sands or oil sands, more particularly to the use of microwaves in the oil recovery.

BACKGROUND ART

Canadian tar sands, commonly called oil sands, are a combination of clay, sand, water, and bitumen, heavy black viscous oil. Oil sand, as mined commercially, typically contains an average of 10-12% bitumen, 83-85% mineral matter and 4-6% water. A film of water coats most of the mineral matter, and this property permits extraction by a hot-water process.

The hot water process is a common commercial process used for extracting bitumen from mined oil sands. The oil sand is put into massive rotating drums and slurried with hot water (50-80° C.) and some steam. Droplets of bitumen separate from the grain of sand and attach themselves to tiny air bubbles. Conditioned slurry is passed through a screen to remove rocks and large pebbles and pumped into large, conical separation vessels where a froth of bitumen is skimmed from the top containing about 60% bitumen, 30% water and 10% solids. The coarse sand settles and is pumped to disposal sites. Some of the smaller bitumen and mineral particles remain in an intermediate water layer called middlings and are pumped to separation vessels. Approximately 90% of the bitumen in the mined oil sands is typically recovered.

The recovered bitumen generally needs to be upgraded to convert the heavy viscous bitumen to a form which can be transported in existing pipeline systems and to ensure an upgraded crude quality which will permit existing refineries to meet anticipated market product demand. The Flexicoking™ followed by hydro-treating of the coker liquids is typically the preferred upgrading process in Canadian tar sand operation.

The production of one barrel of synthetic crude (upgraded bitumen) through the hot water process typically requires about 4.5 barrels of water. Almost all of the water withdrawn for oil sands operations ends up in tailings ponds. Both primary and final extraction plant tailings are pumped to the retention pond for storage.

When these effluent streams containing bitumen, naphtha, water, and solids are discharged to the pond, a portion of the residual bitumen and diluents naphtha floats to the surface of the pond. The dense sand fraction present in the primary stream settles rapidly but the lighter water fines suspension settles very slowly, forming a zone of sludge. After a period of settling a shallow layer of relatively clear water develops near the surface of the pond. Water from this layer is recycled to the extraction process. But the majority of water remains in this sludge, a water-bitumen-fine solids emulsion that is very difficult to break.

The processing of bitumen into synthetic crude through the hot water process requires energy, and this energy is usually generated by burning natural gas which releases greenhouse gas. For example, the production of 1 barrel of synthetic oil may necessitate approximately 1.0 to 1.25 gigajoules of energy and can lead to the release of more than 80 kg of greenhouse gases into the atmosphere.

Thus, the hot water process can lead to problems due to large water requirements, disposal of large tailing ponds, greenhouse gas production and large requirements of energy are major problems facing the oil sand industry.

As such, improvements in the extraction of oil from oil sand or tar sand are desirable.

SUMMARY

It is therefore an aim of the present invention to provide an improved process and system for recovery of oil from tar sand.

In one aspect of the invention there is provided a process for recovering an oil from a tar sand, the process comprising the steps of drying the tar sand to produce a dried tar sand, mixing the dried tar sand with a microwave absorbent to produce a mixed sand, and cracking the mixed sand with microwaves to produce an oil vapor product containing the oil.

In another aspect of the invention there is provided a system for recovering oil from tar sand comprising a tar sand dryer removing water from the tar sand and producing a dried tar sand, a mixing section connected to the dryer to receive the dried tar sand and mixing the dried tar sand with a microwave absorbent to produce a mixed sand, and a microwave cracker connected with the mixing section to receive the mixed sand, the cracker including a microwave guide directing microwaves to the mixed sand, the cracker cracking the mixed sand with the microwaves to obtain a processed sand and an oil vapor product containing the oil.

Further aspects of the invention will be brought out in the following portions of the specification, wherein the detailed description is for the purpose of fully disclosing preferred embodiments of the invention without placing limitations thereon.

BRIEF DESCRIPTION OF THE DRAWINGS

Reference will now be made to the accompanying drawings, showing by way of illustration a particular embodiment of the present invention and in which.

DETAILED DESCRIPTION OF PARTICULAR EMBODIMENTS

Figure 1:
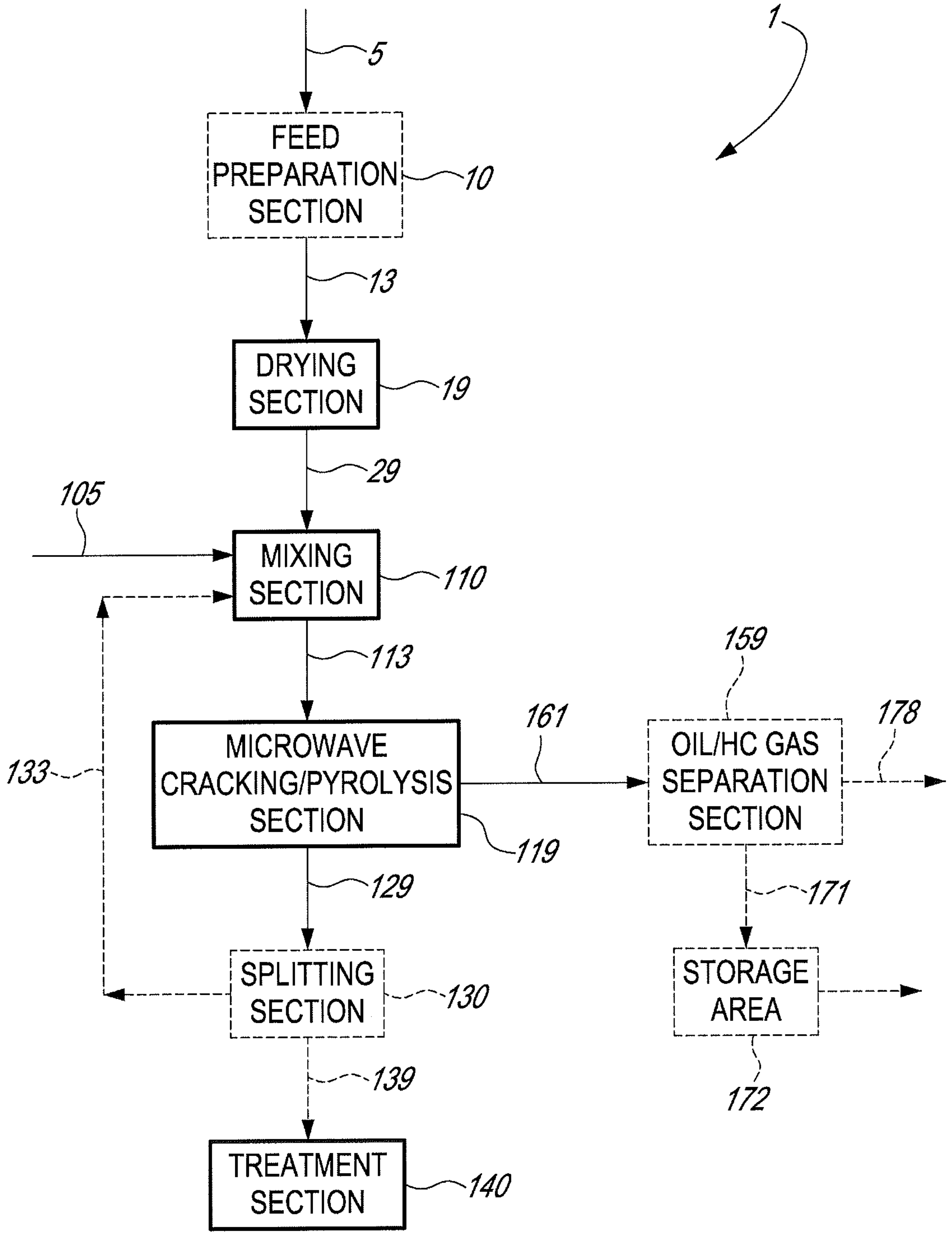
FIG. 1 is a block diagram of the process for recovering oil for tar sand according to one embodiment of the present invention.

The terms "cracking" and "pyrolysis" are used as synonyms herein and refer to a chemical process that reduces complex longer chain hydrocarbons into shorter and lighter hydrocarbons that are generally more useful products, through a thermally activated decomposition reaction. The term "cracker" is understood as the reactor where this pyrolysis reaction occurs.

In the present application, microwaves are used to crack or pyrolize, and optionally dry, the tar sands. The electromagnetic frequency spectrum is usually divided into ultrasonic, microwave, and optical regions. The microwave region is from 300 megahertz (MHz) to 300 gigahertz (GHz) and encompasses frequencies used for much communication equipment. Often the term microwaves or microwave energy is applied to a broad range of radiofrequency energies particularly with respect to the common heating frequencies, 915 MHz and 2450 MHz. The former is often employed in industrial heating applications while the latter is the frequency of the common household microwave oven and therefore represents a good frequency to excite water molecules. In this writing the term “microwave” or “microwaves” is generally employed to represent “radiofrequency energies selected from the range of about 500 to 5000 MHz”, since in a practical sense this large range is employable for the subject invention, although in practice frequencies of 915 and 2450 MHz are preferably used in order to comply with Federal Telecommunication regulation.

The absorption of microwaves by the energy bands, particularly the vibrational energy levels, of atoms or molecules results in the thermal activation of the non-plasma material and the excitation of valence electrons. Microwaves lower the effective activation energy required for desirable chemical reactions since they can act locally on a microscopic scale by exciting electrons of a group of specific atoms in contrast to normal global heating which raises the bulk temperature. Further this microscopic interaction is favored by polar molecules whose electrons become easily locally excited leading to high chemical activity; however, non-polar molecules adjacent to such polar molecules are also affected but at a reduced extent. An example is the heating of polar water molecules in a common household microwave oven where the container is of non-polar material, that is, microwave-passing, and stays relatively cool.

In this sense microwaves are often referred to as a form of catalysis when applied to chemical reaction rates; thus, in this writing the term “microwave catalysis” refers to “the absorption of microwave energy by carbonaceous materials when a simultaneous chemical reaction is occurring”.

Therefore, a microwave absorbent as defined herein is a material that absorbs microwave energy. The microwave absorbent has been found to help initiate pyrolysis of the longer chain hydrocarbons, such as bitumen, found in tar sand. Thus, the microwave absorbent as defined herein is a pyrolysis initiator or catalyst that activates this chemical process.

It is to be noted that the terms “tar sand” and “oil sand” are used as synonyms herein. A tar sand or oil sand is understood to be a carbonate rock impregnated with a wide variety of heavy hydrocarbons. The tar sand includes bitumen, thus is bituminous sand. Bitumen has a varying elemental composition that can be, for example:

80-90 wt % C
8-12 wt % H
0-6 wt % S
0-2 wt % O, and
0-1 wt % N.

Bitumen typically further includes heavy metals such as Ni, V, Pb, Cr, Hg, As, Se as well as other elements. Bitumen also typically includes asphaltenes and metalloporphyrins, compounds that include polar bonds and associated metallic elements that are believed to be points at which microwaves may act at a molecular level to cause the pyrolysis or cracking of the tar sand. Although it is believed that these sites may assist pyrolysis, they are not very effective points of microwave absorption, and hence the need for a microwave absorbent to initiate the pyrolysis reaction.

The term “drying” as used herein is understood as the removal of water from the tar sand by evaporation. As has been described, tar sand has a water content that is typically between 4 and 6% by weight. The term “drying” is furthermore understood to mean that a reduction of water within the tar sand has occurred to a level where the amount of water remaining in the tar sand does not adversely affect the subsequent pyrolysis reaction of the tar sand. Typically, the “drying” step herein reduces water to a level to less than or equal to 0.5% by weight, more preferably to less than or equal to 0.2% by weight. At a water level of 0.5% by weight or below in the tar sand, the tar sand is considered as being essentially free of humidity, or “dry”.

Referring to FIG. 1, a system 1 for recovery of oil from tar sand according to a particular embodiment of the present invention is schematically illustrated. The process of recovery of oil from tar sand with the system 1 begins with the mining and transport of a mined tar sand 5 to a tar sand feed preparation section 10. In the feed preparation section 10 the mined tar sand 5 is crushed and ground to a size that allows for easier drying and pyrolysis to produce a tar sand feed 13. Alternately, the feed preparation section 10 can be omitted if the mined tar sand already has a size that allows for easy drying and pyrolysis.

The prepared tar sand feed 13 is sent to a drying section 19, where the majority of the water in the tar sand is removed to produce a dried tar sand 29, e.g. a tar sand including preferably less than 0.5% by weight of water, and more preferably to less than or equal to 0.2% by weight of water. As will be further detailed below, the drying section may use microwaves to dry the tar sand, although alternates method of drying may also be used.

The drying section 19 helps to markedly minimize the amount of water used in the process, and as such is in stark contrast to the usual hot water process for oil recovery from tar sand that uses large amount of water to suspend the oil. The drying section 19 allows for recovery of water which is relatively clean for other uses.

The dried tar sand 29 enters a mixing section 110 where it is mixed with a microwave absorbent from a initiator stream 105 and/or a recirculated stream 133 (to be further discussed below) to produce a mixed sand 113. In a particular embodiment, the microwave absorbent includes carbon, activated carbon, silicon carbide, other microwave absorbents or mixtures thereof. The microwave absorbent serves as a pyrolysis initiator for the dried tar sand 29.

The mixed sand 113 is conveyed to a microwave cracking or pyrolysis section 119. As will be further detailed below, the cracking process uses microwaves to activate the microwave absorbent and heat the mixed sand 113 to initiate pyrolysis. Because the tar sand has been dried by the drying section 19 before entering the cracking or pyrolysis section, the production of a bitumen-water emulsion during pyrolysis is minimized or avoided. The microwave cracking or pyrolysis section 119 produces two outputs: a processed sand 129 and an oil vapor product 161. The processed sand 129 includes the inorganic particulate matter (mineral matter) found in the mined tar sand 5 and a residual carbon produced during the cracking process.

It should be noted that if a microwave absorbent is available at an acceptable cost, the initiator stream 105 of microwave absorbent may be used to fulfill the process requirement for microwave absorbent, i.e. the recirculated stream 133 is omitted, and the processed sand 129 is circulated directly to a treatment section 140. However, in the particular embodiment shown, the initiator stream 105 is used only for start-up of the cracking process, before carbon is present in the processed sand 129. As such, the processed sand 129 is split into two streams in a splitting section 130, to produce the recirculated stream 133 which is added to the mixing section 110 and a residual stream 139 which purges the excess carbon and sand from the system. The processed sand of the recirculated stream 133 acts as a microwave absorbent because of the residual carbon contained therein. Due to the high temperatures of the cracking process, the recirculated processed stream 133 increases or maintains the temperature of the dried tar sand that enter the mixing section 110. The residual processed sand stream 139 may be combusted in a fluidized bed boiler to burn the residual carbon and produce steam for power production, steam generation, preheating the tar sand for water removal, etc in the treatment section 140. If sulfur is present in the processed sand 129, adding limestone or CaO to the fluidized bet reduces sulfur emissions from the boiler. Clean sand and calcium sulfate are removed from the fluidized bed boiler for disposal.

It one embodiment, the oil vapor product 161 from the cracking/pyrolysis section 119 is sent directly to processing in a refinery where the oil and hydrocarbon gas can be separated. Optionally, the oil vapor product 161 is circulated to an oil/hydrocarbon gas separation section 159, where it is cooled to condense and separate the oil 171 from the hydrocarbon gas stream 178. The recovered oil liquid 171 that condensed in the oil/hydrocarbon gas separation system 159 is stored in appropriate tanks in a storage area 172 before being pumped to a pipeline or to a specific use. The hydrocarbon gas stream 178 may be used for electrical generation, in mine vehicles or be further processed in a refinery.

Figure 2:
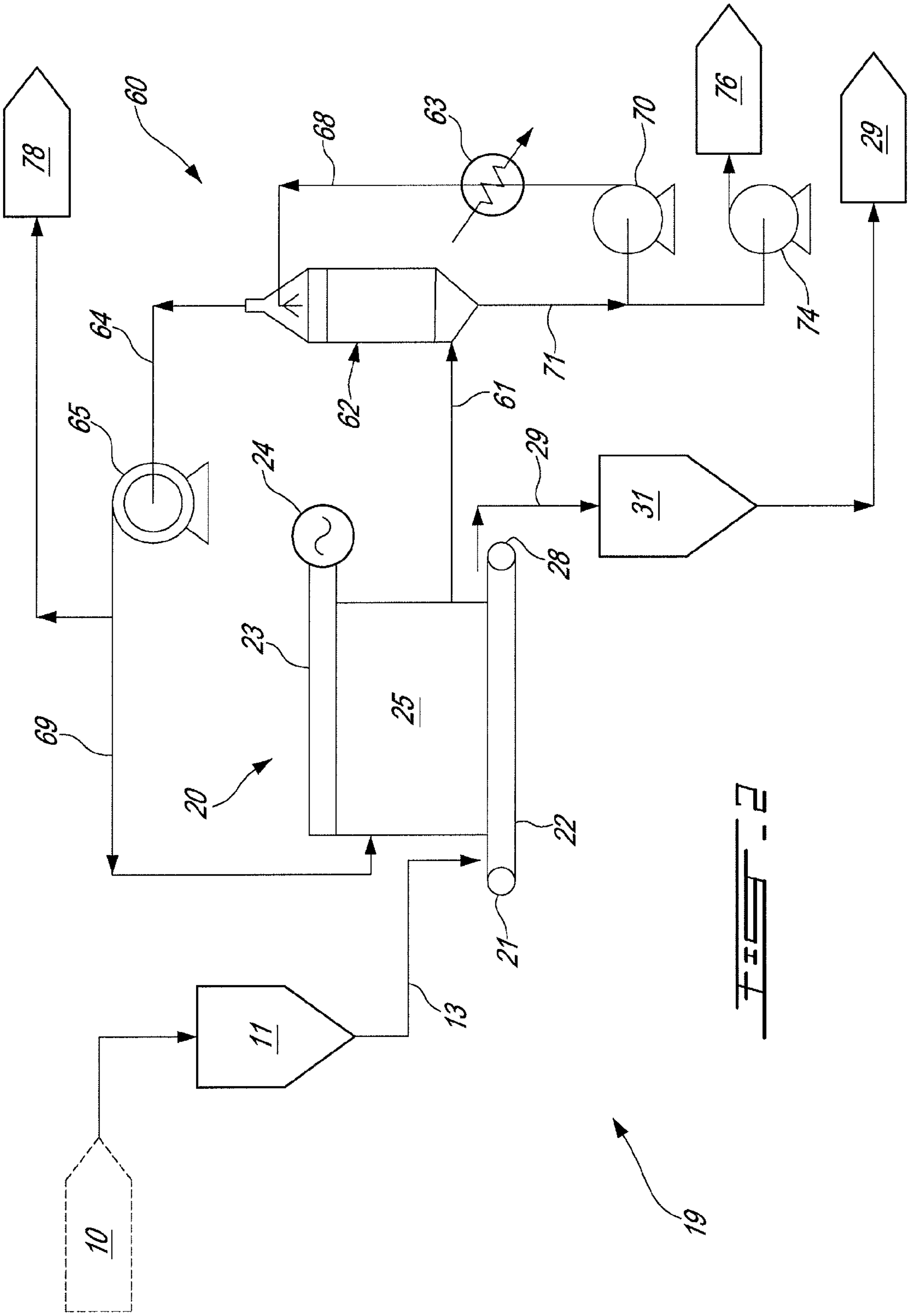
FIG. 2 is a process flow diagram of a microwave drying system for tar sand according to one embodiment of the present invention.
Figure 3:
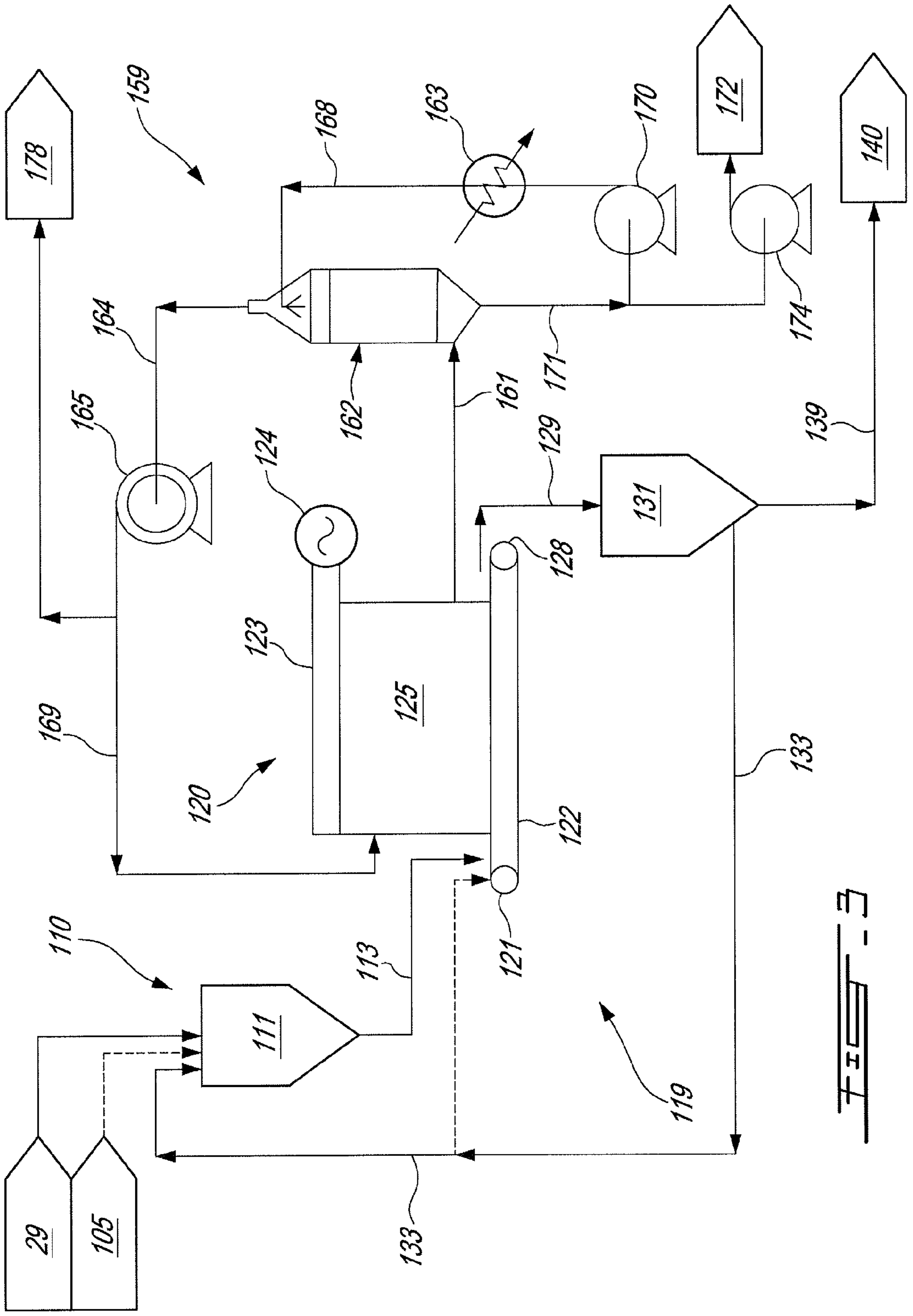
FIG. 3 is a process flow diagram for the microwave pyrolysis reactor system according to one embodiment of the present invention.

A particular embodiment of the system for the recovery of oil from tar sand 1 is presented in more details FIG. 2 and FIG. 3. It will be appreciated that the process and apparatus presented may vary as to configuration and as to details of the parts, and that the process may vary as to the specific steps and sequence, without departing from the basic concepts as disclosed herein.

FIG. 2 shows part of the system 1 according to a particular embodiment, including the drying section 19. Mined tar sand is crushed and screened in the feed preparation section 10 to prepare it for the drying section 19. The prepared tar sand feed is transported from the feed preparation section 10 to a feed hopper 11, and then to the drying section through a conveyor (not shown). In a particular embodiment the conveyor for the tar sand stream 13 is a screen conveyor or screw conveyor.

Although it is possible to dry the tar sand with only heat, in a particular embodiment of the invention the drying section 19 includes a microwave dryer 20. The prepared tar sand 13 is fed to an inlet 21 of the microwave dryer 20. The dryer 20 includes a conveyor 22 that transports the tar sand through the dryer housing 25. A microwave guide 23 directs microwaves emitted by a microwave source 24 at the tar sand being conveyed through the tunnel defined by the housing 25, to evaporate the water contained therein.

In an alternate embodiment, the dryer 20 dries the tar sand in batches instead of in a continuous flow, i.e. the conveyor 22 is omitted. The dryer 20 receives a predetermined quantity of tar sand which remains in place within the housing 25 until the desired water content is reached.

When the tar sand enters the microwave drying reactor 20, process conditions in the reactor are regulated such that the water in the tar sands absorbs microwave energy and evaporates rapidly. Water vapor and mist are carried by the recycled air stream and collected in the condenser. Since sand and bitumen do not absorb microwave energy as intensely as water, the temperature of dried tar sand does not increase above the water boiling point and bitumen pyrolysis is not initiated.

The dryer 20 may also include a convective system or air sweep, to accelerate drying of the tar sand with the assistance of a compressor 65. This circulation of gas is illustrated in a same direction as the movement of the conveyor but alternately may be in a countercurrent direction.

The dryer 20 discharges the dried tar sand 29 from a dryer outlet 28 into a dried tar sand hopper 31 before circulation to the cracking and pyrolysis section 119. In an alternate embodiment, the hopper 31 is omitted and the dried tar sand 29 circulates directly to the pyrolysis section, for example through a conveyor.

In an alternate embodiment, the microwave dryer 20 is omitted, and the drying section 19 includes a mechanism to heat the tar sand 13 on the conveyor by using heat from an electricity generation system to remove the water therefrom. Again, the tar sand is heated to a temperature of preferably about 300° F. such as to remove the water without initiating pyrolysis. In another alternate embodiment, part of the water is removed by preheating the tar sand with heat from the electricity generation system on the screen conveyor transporting the tar sand 13 and the remaining water is removed with the microwave dryer 20.

In one embodiment, the wet gas 61 from the dryer 20 which includes the water vapor is released to the atmosphere. In the embodiment shown, the drying section 19 includes a dryer gas treatment portion 60 to which the wet gas 61 of the dryer 20 including the water vapor produced during the drying process is circulated.

The dryer gas treatment portion 60 comprises a contact vapor/liquid separator 62 which condenses the wet dryer gas 61 withdrawn from the dryer housing 25 and produces a dried gas 64 which enters the suction side of the blower/compressor 65. On the pressure side of the blower/compressor 65 a portion of the air stream is purged 78 and another portion 69 is returned to the dryer 20 to define the convective system or air sweep of the dryer 20.

The condensed water 71 is at least partially purged from the vapor/liquid separator 62 via a water pump 74 that sends the stream to discharge or treatment 76. Since the water is extracted from the tar sand prior to the cracking of the bitumen, the water requires only minor treatment to be used in other operations.

Although any adequate type of vapor/liquid separator 62 can be used, in the embodiment shown, part of the condensed water 71 is recirculated from the base of the vapor/liquid separator 62 by a recirculation pump 70 to go through a heat exchanger 63 for cooling. The cooled circulating water 68 produced is circulated to the vapor/liquid separator 62 where it contacts the wet hot dryer gases 61 and produces the condensation.

FIG. 3 shows another part of the system 1 according to a particular embodiment. Since sand and bitumen do not absorb microwave energy as intensely as water, the temperature of dried tar sand would not increase significantly and bitumen pyrolysis would not be initiated as long as temperature within the dried tar sand remained below the temperature of pyrolysis of bitumen. Therefore the dry tar sand is activated with the addition of a pyrolysis initiator in the form of a microwave absorbent.

Many types of particulate solid mixers can be envisaged to combine the dried tar sand 29 from the drying section 19 and the microwave absorbent from the initiator stream 105 and/or the recirculated stream 133. In the embodiment shown, the mixing section 110 includes a hopper 111 as a mixing platform and receiving the dried tar sand 29 from the drying section 19, and the initiator stream 105 and/or recirculated stream 133. In a particular embodiment, the mixing section 110 also includes conveyors that ensure a homogeneous distribution of microwave absorbent and dried tar sand to the cracking/pyrolysis section 119. In a particular embodiment, the ratio between the quantity of dried tar sand 29 and the quantity of microwave absorbent, i.e. recirculated processed sand of the recirculated stream 133 or material of the initiator stream 105, is from 1 to 5, and preferably 5, i.e. there is from 1 and 5, and preferably 5, parts of dried tar sand 29 for each part of the recirculated stream 133 or initiator stream 105. The mixing section 110 produces a mixed sand 113 that is ready for pyrolysis.

In an alternate embodiment, the mixing section 110 is incorporated in the cracker 120 of the cracking/pyrolysis section 119, and the microwave absorbent 105 and/or 133 is added at the inlet 121 thereof together with the dried tar sand 29 in an appropriate proportion sufficient to pyrolize the tar sand.

The cracking/pyrolysis section 119 includes a microwave cracker 120 where the mixed sand 113 is fed through a cracker inlet 121. The cracker 120 includes a conveyor 122, which in a particular embodiment is a screen conveyor, which transports the mixed sand 113 through the cracker housing 125. A microwave guide 123 directs microwaves emitted by a microwave source 124 at the mixed sand being conveyed through the tunnel defined by the housing 125. The microwaves activate the microwave absorbent present in the mixed sand 113 and initiate pyrolysis.

In an alternate embodiment, the cracker 120 pyrolizes the mixed sand 113 in batches instead of in a continuous flow, i.e. the conveyor 122 is omitted. The cracker 120 receives a predetermined quantity of mixed sand which remains in place within the housing 125 until the desired level of pyrolysis is reached.

The unique characteristics of microwave energy are utilized to significantly enhance pyrolysis reactions of bitumen. When the bitumen starts to be pyrolized, it absorbs microwaves and the pyrolysis rate accelerates significantly. The bitumen is decomposed into oil, gas, and carbon by microwaves. The pyrolized dried tar sand, because of the residual carbon contained therein, is an excellent microwave absorbent, and its temperature increases rapidly when exposed to microwaves. The recycled processed sand 133 thus contains this residual carbon and initiates bitumen pyrolysis when the mixed sand 113 is subjected to microwaves. Once the bitumen pyrolysis begins, the pyrolysis products absorb microwaves and accelerate the reaction significantly. The rate of microwave-induced pyrolysis is an order of magnitude greater than the conventional thermal pyrolysis rate.

Process conditions in the cracker 120 are regulated such that the bitumen of the tar sands absorbs microwave energy is cracked rapidly. The temperature of the cracker 120 is maintained above that of the dryer 20. In a preferred embodiment the temperature within the cracker is regulated above 300° F., and more preferably at least about 500° F. The pyrolysis is controlled through variation of the microwave field strength.

The cracker 120 discharges the processed sand 129 from a cracker outlet 128 into a processed sand hopper 131, which in a particular embodiment may be omitted. Through the splitting section 130, which in the embodiment shown is provided in the hopper 131, the processed sand 129 is separated into the recirculated stream 133 and the residual stream 139. The recirculated stream 133 is recirculated to the feed hopper 111 of the cracking/pyrolysis section 119 via a conveyor (not illustrated), or alternately back to the inlet 121 of the cracker 120 directly. The residual processed sand 139 may be subject to further processing or disposal in the treatment section 140.

The oil/hydrocarbon gas separation section 159 comprises an oil/gas separator 162 which condenses the oil vapor product 161 withdrawn from the cracker housing 125 and produces a hydrocarbon gas 164 which enters the suction side of a blower/compressor 165. On the pressure side of the blower/compressor 165 a portion of the gas stream is purged 178, for example for electricity generation and/or for use on site in vehicles in the mining operation, and another portion 169 is returned to the cracker 120 as a sweep gas. Although the circulation of gaseous hydrocarbons is illustrated in a same direction as the movement of the conveyor, alternately the circulation may be in a countercurrent direction.

The condensed oil 171 is at least partially purged from the separator 162 via a pump 174 that sends the stream to storage 172. The produced oil is light and can be transported by existing pipe line to the refinery.

Although any adequate type of oil/gas separator 162 can be used, in the embodiment shown, part of the condensed oil 171 is recirculated from the base of the oil/gas separator 162 by a recirculation pump 170 to go through a heat exchanger 163 for cooling. The cooled circulating oil 168 produced is circulated to the oil/gas separator 162 where it contacts the oil vapor product 161 and produces the condensation.

The above described process and system allow for water to be removed from the tar sand prior to the oil production, thus eliminating or substantially reducing the size of tailing ponds and avoiding the production of water-bitumen-finer solids emulsion. Process water removed from the tar sand advantageously requires only minor treatment as it contains no significant amount of organics. The process and system allow for bitumen to be cracked to produce transportable oil, while the produced gas can be used to produce electric power, using fuel cells, that allows for lower green house emissions.

In a preferred embodiment the main material of construction of the reactors 20, 120 is a stainless steel. In particular, for the cracker 120, the stainless steel is one that is appropriate for a higher temperature service of pyrolysis.

Example 1

A laboratory microwave apparatus was used to pyrolize Athabasca oil sand that contained 8% of bitumen by weight. The following is the product distribution as a weight percent of the bitumen from this microwave experiment:

| | |
|---|---|
| Oil | 56.1% |
| Gas | 22.0% |
| Carbon | 21.9% |

The distribution of bitumen pyrolysis products shown above is similar to the product distribution from the pyrolysis of the kerosene in oil shale at 752° F. as shown below:

| | |
|---|---|
| Oil | 56.7% |
| Gas | 16.4% |
| Carbon | 26.9% |

An estimate of the energy requirements and production potential is calculated based on 2,000 lbs (1 ton) of oil sand containing 12% bitumen and 4% water.

Oil—134.64 lbs (17.57 gallons)
Hydrocarbon Gas—52.8 lbs
Residual Carbon—52.56 lbs
Water removed—80 lbs
Distribution of Energy Potential
Oil 2,339,774 BTU
Gas 917,558 BTU
Carbon 735,840 BTU
Total 3,993,172 BTU Energy required for water removal and oil and gas recovery:

Water Evaporation 92,160 BTU

Bitumen pyrolysis 330,188 BTU

Total Energy 422,354 BTU

Microwave process energy requirement 124 kWh

Total microwave electricity requirement (80% microwave efficiency) 155 kWh

On site electricity production potential

Hydrocarbon gas (50% CCGT generation efficiency) 134 kWh

Residual carbon (33% steam generation efficiency) 72 kWh

Total electricity production potential 206 kWh

Electricity available for other mining requirements 51 kWh

The waste heat from electric generation systems is used to preheat oil sands before dehydration; electricity requirements for microwave water removal are reduced. A portion of hydrocarbon gas can also be used for internal combustion engines in mining vehicles.

The embodiments of the invention described above are intended to be exemplary. Those skilled in the art will therefore appreciate that the foregoing description is illustrative only, and that various alternate configurations and modifications can be devised without departing from the spirit of the present invention. Accordingly, the present invention is intended to embrace all such alternate configurations, modifications and variances which fall within the scope of the appended claims.

The invention claimed is:

1. A process for recovering an oil from a tar sand, the process comprising the steps of:

drying the tar sand to produce a dried tar sand;

mixing the dried tar sand with a recirculated sand to produce a mixed sand, the mixed sand containing a ratio of from 1 to 5 parts of dried tar sand for each part of the recirculated sand;

exposing the mixed sand to microwaves;

increasing a temperature of the mixed sand through microwave absorption by the recirculated sand, the temperature of the mixed sand increasing at a higher rate than that of a same quantity of the dried tar sand exposed to the same microwaves;

cracking the heated mixed sand with the microwaves to produce an oil vapor product containing the oil and a processed sand; and recirculating part of the processed sand as the recirculated sand into the dried tar sand.

2. The process of claim 1, further comprising condensing the oil vapor product to extract the oil in a liquid form.

3. The process of claim 1, wherein the process further comprises using another part of the processed sand in a combustion process to produce heat, steam and/or electricity.

4. The process of claim 1, wherein the oil vapor product contains a hydrocarbon gas, the process further comprising recirculating at least part of the hydrocarbon gas to the cracking step.

5. The process of claim 1, wherein the oil vapor product contains a hydrocarbon gas, the process further comprising burning the hydrocarbon gas to produce electricity.

6. The process of claim 1, wherein drying the tar sand includes reducing a water content of the tar sand to value of at most 0.5% by weight.

7. The process of claim 1, wherein drying the tar sand is performed using microwaves.

8. The process of claim 1, wherein mixing the dried tar sand with the recirculated sand is performed with the recirculated sand having a higher temperature than that of the dried tar sand such that the mixed sand has a higher temperature than that of the dried tar sand.

9. The process of claim 1, wherein the dried tar sand is mixed with the recirculated sand with a ratio of about 5 parts of dried tar sand for each part of the recirculated sand.

10. A system for recovering oil from tar sand comprising:

a tar sand dryer removing water from the tar sand and producing a dried tar sand;

a mixing section connected to the dryer to receive the dried tar sand and mixing the dried tar sand with a recirculated sand to produce a mixed sand;

a microwave cracker connected with the mixing section to receive the mixed sand, the cracker including a microwave guide directing microwaves to the mixed sand, the cracker increasing a temperature of the mixed sand through microwave absorption by the recirculated sand, and cracking the heated mixed sand with the microwaves to obtain a processed sand and an oil vapor product containing the oil; and a recirculation connection between an outlet of the cracker and the mixing section, the recirculation connection conveying part of the processed sand as the recirculated sand to the mixing section, the recirculation connection being sized to convey a quantity of the processed sand to the mixing section defining a ratio of from 1 to 5 parts of dried tar sand for each part of the recirculated sand.

11. The system of claim 10, further comprising a splitting section receiving the processed sand from the cracker, the splitting section separating the processed sand into a first stream directed to the recirculation connection and a second stream directed to a fluid bed burner to produce heat, steam and/or electricity from a residual carbon in the processed sand.

12. The system of claim 10, further comprising an oil/hydrocarbon gas separation section withdrawing and condensing the oil vapor product from the cracker to recover the oil.

13. The system of claim 12, wherein the oil/hydrocarbon gas separation section includes a vapor/liquid separator separating the oil vapor product to produce the oil in a liquid form and a hydrocarbon vapor, and a compressor directing at least part of the hydrocarbon vapor to an electrical generator to produce electricity.

14. The system of claim 12, wherein the oil/hydrocarbon gas separation section includes a vapor/liquid separator separating the oil vapor product to produce the oil in a liquid form and a hydrocarbon vapor, and a compressor returning at least part of the hydrocarbon vapor to the cracker.

15. The system of claim 10, wherein the dryer is a microwave dryer comprising a microwave guide directing microwaves to the tar sand, the dryer drying the tar sand with the microwaves to obtain the dried tar sand and water vapor.

* * * * *